United States Patent
Chang et al.

(10) Patent No.: US 9,567,315 B1
(45) Date of Patent: Feb. 14, 2017

(54) METHOD FOR SYNTHESIS OF 4-OH SUBSTITUTED ANABASEINE DERIVATIVE

(71) Applicant: INSTITUTE OF NUCLEAR ENERGY RESEARCH, ATOMIC ENERGY COUNCIL, EXECUTIVE YUAN, R.O.C., Taoyuan (TW)

(72) Inventors: Yu Chang, Taoyuan (TW); Cheng-Fang Hsu, Taoyuan (TW)

(73) Assignee: Institute of Nuclear Energy Research, Atomic Energy Council, Executive Yuan, R.O.C., Taoyuan (TW)

( * ) Notice: Subject to any disclaimer, the term of this patent is extended or adjusted under 35 U.S.C. 154(b) by 0 days.

(21) Appl. No.: 15/136,066

(22) Filed: Apr. 22, 2016

(51) Int. Cl.
*C07D 213/30* (2006.01)
*C07D 401/04* (2006.01)

(52) U.S. Cl.
CPC .................... *C07D 401/04* (2013.01)

(58) Field of Classification Search
CPC .................................... C07D 213/30
USPC ........................................ 546/258
See application file for complete search history.

(56) References Cited

PUBLICATIONS

Ikeda et al., "3-(4-Hydroxybenzyldines), etc.," J. Pestic. Sci. 34(2), 96-99 (2009).*

\* cited by examiner

*Primary Examiner* — Patricia L Morris
(74) *Attorney, Agent, or Firm* — Rosenberg, Klein & Lee

(57) ABSTRACT

A method for synthesis of 4-OH substituted anabaseine derivative which is used as an $\alpha_7$ receptor agonist is revealed. A nucleophilic substitution reaction of δ-valerolactam with ethyl nicotinate is carried out to get an intermediate product. Then heat the intermediate product under reflux with concentrated hydrochloric acid to get a cyclized product-anabaseine. Next anabaseine and 4-hydroxyethoxy-2-methoxybenzaldehyde are reacted under concentrated hydrochloric acid catalysis to get a 4-OH anabaseine derivative 3-[(4-Hydroxyethoxy-2-methoxy)-benzylidene]anabaseine. The 4-OH anabaseine derivative is synthesized and prepared easily by the present invention. Not only the steps for synthesis are simplified, the yield is as high as 60%. The product can be mass-produced.

14 Claims, 1 Drawing Sheet

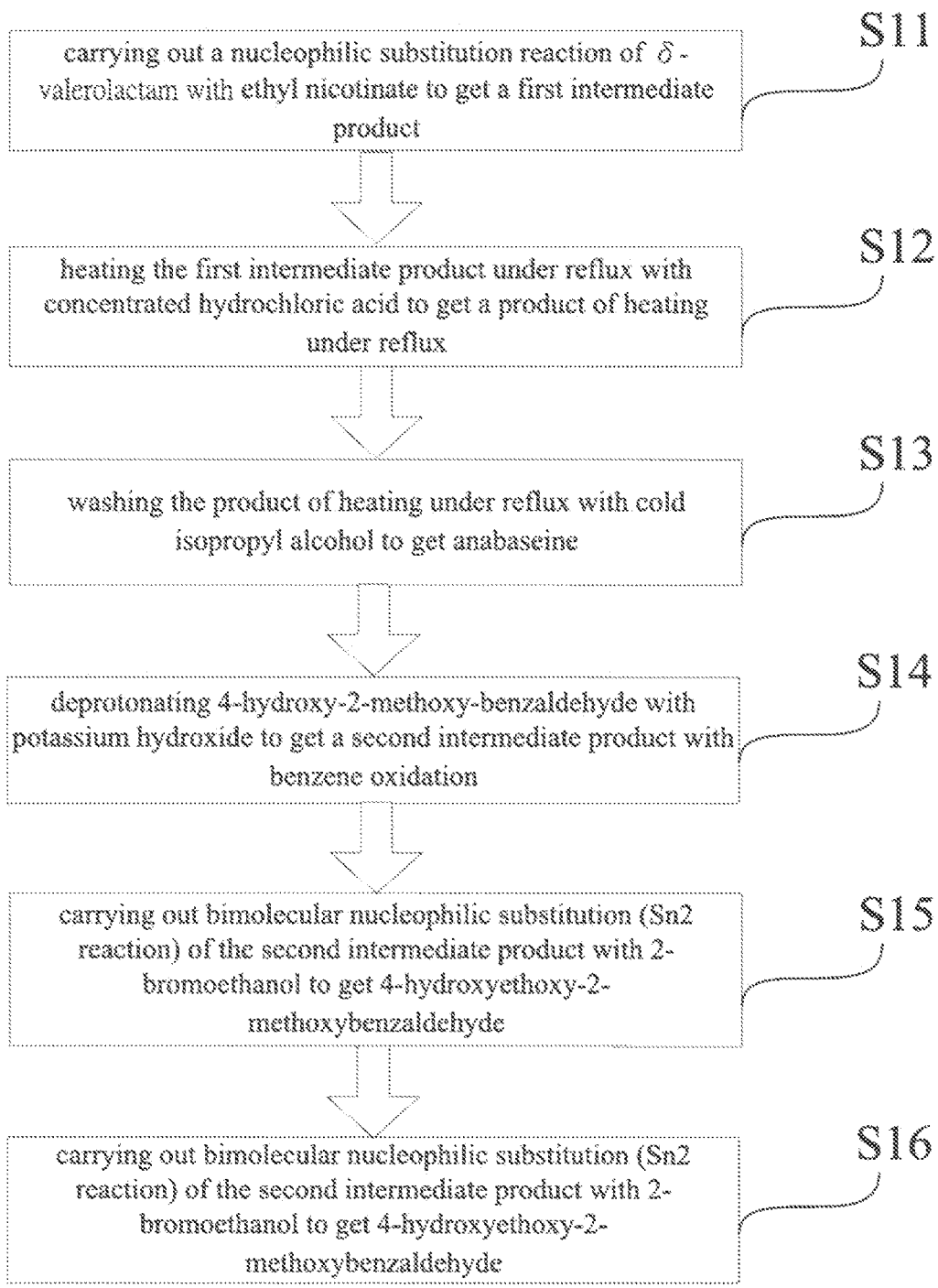

METHOD FOR SYNTHESIS OF 4-OH SUBSTITUTED ANABASEINE DERIVATIVE

BACKGROUND OF THE INVENTION

Field of the Invention

The present invention relates to a method for synthesis of anabaseine derivatives, especially to a method for synthesis of 4-OH substituted anabaseine derivative.

Descriptions of Related Art

Acetylcholine is a neurotransmitter released by nerve cells of central and peripheral nervous systems for intercommunication between the nervous system and the immune system. The nervous system sends signals through acetylcholine for inhibition of inflammatory processes. Acetylcholine works by binding to receptors located on surface of cells such as neurons or immune cells. There are two main classes of acetylcholine receptor, muscarinic (M) and nicotinic (N).

Nicotine can mimic the action of acetylcholine at acetylcholine receptors and bind to acetylcholine receptors as an agonist of the Alpha-7($\alpha_7$) nicotinic acetylcholine receptor. Thus some research shows that nicotine is promising for the treatment of cranial nerve diseases such as Alzheimer's disease, Parkinson's disease, and Tourette syndrome. In some patients, their learning abilities are even recovered. Moreover, nicotine also activates $\alpha$-7 nicotinic acetylcholine receptors on macrophages and suppresses release of pro-inflammatory cytokines. Thus nicotine acts as an anti-inflammatory agent in patients with ulcerative colitis, Kaposi's sarcoma epilepsy and asthma.

However, nicotine is highly toxic and addictive, and is associated with cardiovascular disease, cancer, etc. Thus nicotine is unable to be used as a drug due to its harmful effects. A series of drugs with similar structure of nicotine have been developed to provide pharmaceutical effects similar to nicotine without toxic effect. Anabaseine is a representative of these drugs.

Anabaseine is an Alpha-7 nicotinic acetylcholine receptor agonist and initially designed for treatment of Alzheimer's disease. It improves cognitive functions of the Alzheimer's patients, without poisoning and addiction of nicotine. In the research now, anabaseine is modified in order to enhance its pharmacological properties. 4-OH-anabesine has the most healing effect among the anabaseine derivatives.

Among the techniques available now, 4-OH-anabesine is synthesized by reflux of anabaseine and 4-hydroxyethoxy-2-methoxybenzaldehyde with catalysis of concentrated hydrochloric acid. The final product obtained is a 4-OH substituted anabaseine derivative named 3-[(4-Hydroxy-ethoxy-2-methoxy)-benzylidene]anabaseine. The anabaseine used is prepared by nucleophilic substitution reaction of δ-valerolactam with ethyl nicotinate. The intermediate product, lithium 3-nicotinoyl-2-piperidone enolate, is obtained. Then the intermediate product is heated under reflux with concentrated hydrochloric acid to get cyclized product-anabaseine. The cyclized product is filtered and washed with solvents.

Yet anabaseine is easy to dissolve in solvents such as water under normal temperature. Thus anabaseine is easy to be lost during the washing step and the yield is dropped to 20-30%. Moreover, TLC test and Proton Nuclear Magnetic Resonance (1H NMR) show that there are still some by-products after substitution of 4-OH group. Thus the elution time is quite long while using column chromatography for separation. The yield of column chromatography is only about 40%-50%, a bit insufficient. Thus there is room for improvement.

SUMMARY OF THE INVENTION

Therefore it is a primary object of the present invention to provide a method for synthesis of 4-OH substituted anabaseine derivative which prevent loss of the target product effectively and increase yield of the target product.

It is another object of the present invention to provide a method for synthesis of 4-OH substituted anabaseine derivative that not only simplifies isolation and purifications steps but also increases the production rate of the target product.

In order to achieve the above objects, a method for synthesis of 4-OH substituted anabaseine derivative according to the present invention includes a plurality of steps. First carry out a nucleophilic substitution reaction of δ-valerolactam with ethyl nicotinate to get a first intermediate product. Then heat the first intermediate product under reflux with concentrated hydrochloric acid and wash the product of heating under reflux with cold isopropyl alcohol to get anabaseine. Next deprotonate 4-hydroxy-2-methoxybenzaldehyde with potassium hydroxide to get a second intermediate product with benzene oxidation. Then carry out bimolecular nucleophilic substitution (Sn2 reaction) of the second intermediate product with 2-bromoethanol to get 4-hydroxyethoxy-2-methoxybenzaldehyde. React anabaseine with 4-hydroxyethoxy-2-methoxybenzaldehyde under concentrated hydrochloric acid catalysis to get a crude product. The crude product is dissolved in methanol and precipitated with ether to get a final product.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein:

The FIGURE is a flow chart showing steps of an embodiment of a method for synthesis of 4-OH substituted anabaseine derivative according to the present invention.

DETAILED DESCRIPTION OF THE PREFERRED EMBODIMENT

In order to learn features and functions of the present invention, please refer to the following embodiments together with the FIGURE.

As a representative of 4-OH substituted anabaseine derivative, 3-[(4-Hydroxyethoxy-2-methoxy)benzylidene] anabaseine synthesized by the present invention includes 4-OH substituted group and shows considerable improvement in cognitive function of Alzheimer's patients as an $\alpha_7$ receptor agonist.

Referring to the FIGURE, a method for synthesis of 4-OH substituted anabaseine derivative includes the following steps.

Step S11: carry out a nucleophilic substitution reaction of δ-valerolactam with ethyl nicotinate to get a first intermediate product;

Step S12: heat the first intermediate product under reflux with concentrated hydrochloric acid to get a product of heating under reflux;

Step S13: wash the product of heating under reflux with cold isopropyl alcohol to get anabaseine;

Step S14: deprotonate 4-hydroxy-2-methoxybenzaldehyde with potassium hydroxide to get a second intermediate product with benzene oxidation;

Step S15: carry out bimolecular nucleophilic substitution (Sn2 reaction) of the second intermediate product with 2-bromoethanol to get 4-hydroxyethoxy-2-methoxybenzaldehyde;

Step S16: react anabaseine with 4-hydroxyethoxy-2-methoxybenzaldehyde under concentrated hydrochloric acid catalysis to get a final product.

As shown in step S11, the present method uses δ-valerolactam as an initial reactant that reacts with ethyl nicotinate. Under the action of lithium diisopropylamide (LDA) and trimethylsilyl (TMS), nucleophilic substitution occurs, as shown in the following equation 1:

(Equation 1)

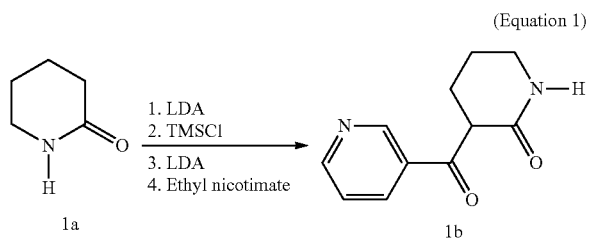 [SMILES: O=C1CCCCN1 ; O=C1NCCCC1C(=O)c1cccnc1]

During the nucleophilic substitution, firstly the hydrogen on the nitrogen of 6-valerolactam is protected by TMS. Then LDA is used to deprotonate the hydrogen on α-carbon to give an anion that is used as a nucleophilic agent and reacting with ethyl nicotinate for nucleophilic substitution. Thus an intermediate product containing a mixture of isomers, enol and ketone, is obtained. The temperature of the reactants added is ranging from −75° C. to −65° C. while −70° C. is preferred. The period required for adding the reactants is ranging from 1 hour to 3 hours while 2 hours are preferred. The reactants are stirred and reacted at room temperature for 16~24 hours while 17 hours are preferred. Thus the first intermediate product is obtained.

Refer to step S12, the first intermediate product obtained in the step S11 is heated under reflux with concentrated hydrochloric acid to get anabaseine. The temperature of the first intermediate product and the concentrated hydrochloric added is 0-4° C., as shown in the following equation 2.

(Equation 2)

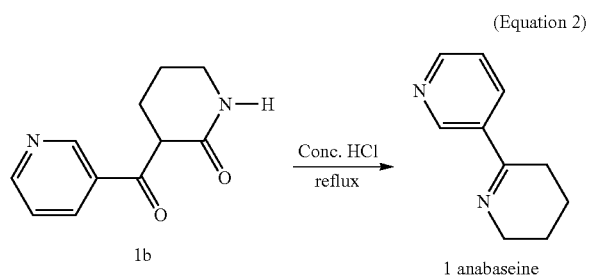 [SMILES: O=C1NCCCC1C(=O)c1cccnc1 ; c1cncc(C2=NCCCC2)c1]

The intermediate product obtained in the previous step is a mixture of isomers, enol and ketone. After reacting with concentrated hydrochloric acid, the two isomers get the same products. At this step, the mixture of the intermediate product is heated under reflux together with concentrated hydrochloric acid. A primary product anabaseine is obtained after reactions of deacidification, nucleophilic addition, cyclization, and dehydration.

Refer to step S13, anabaseine is easily dissolved in water. Thus the use of aqueous solution for filtering results in loss of anabaseine and reduced the yield. In order to prevent this problem, a polar solvent is used to wash the product. Cold isopropyl alcohol is preferred because it removes impurities without loss of the product.

Refer to step S14 and step S15, take 4-hydroxy-2-methoxybenzaldehyde as a reactant. Firstly potassium hydroxide is used as a deprotonating agent for deprotonation of 4-hydroxy group to form a phenoxide intermediate. The equivalent ratio of potassium hydroxide to 4-hydroxy-2-methoxybenzaldehyde is ranging from 4:1 to 1:1 while 2:1 is preferred. During deprotonation, the reactants are suspended in anhydrous alcohol, heated to 90° C.~100° C. and reacted for 0.5~2 hours. The optimal temperature is 95° C. and the preferred reaction time is 1 hour. Then bimolecular nucleophilic substitution (Sn2 reaction) of phenoxide intermediate with 2-bromoethanol is carried out to get 4-hydroxyethoxy-2-methoxybenzaldehyde. The reaction temperature is 90° C.~100° C. and the reaction time is 16~24 hours. The preferred reaction temperature and time are 95° C. and 17 hours respectively. Thus 4-hydroxyethoxy-2-methoxybenzaldehyde, a reactant for synthesis of 4-OH substituted anabaseine derivative, is obtained, as shown in the following equation 3.

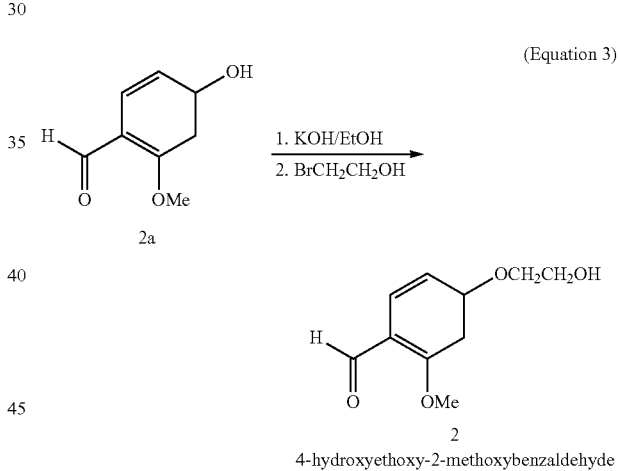

After bimolecular nucleophilic substitution, thin layer chromatography (TLC) test is used to detect whether there is any starting material unreacted. If there is starting material unreacted, column chromatography is used to separate the starting material and the product. A solvent system having n-hexane and ethyl acetate is used for elution. First a starting material is separated and recovered by the solvent of n-hexane and ethyl acetate (1:1). Then 4-hydroxyethoxy-2-methoxy-benzaldehyde is separated and obtained by the solvent with higher polarity formed by n-hexane and ethyl acetate in a ratio of 3:7.

Refer to step S16, anabaseine produced in step S11 to S13 and 4-hydroxyethoxy-2-methoxybenzaldehyde produced in step S14 and S15 are heated to reflux with catalyst of concentrated hydrochloric acid. Thus the final product 3-[(4-Hydroxyethoxy-2-methoxy)benzylidene]anabaseine is obtained, as shown in the following equation 4.

(Equation 4)

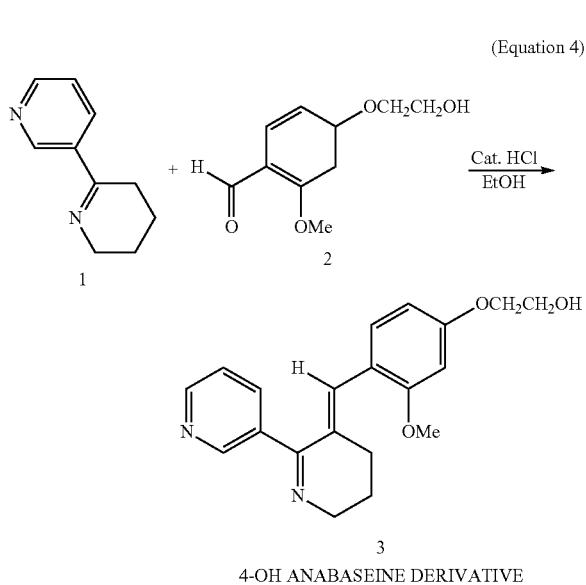

4-OH ANABASEINE DERIVATIVE

In order to remove by products and get the final product with higher purity, the present invention further provides a way to purify the final product. First the crude product obtained by reflux is dissolved in methanol. Then the final product is precipitated with ether. This step can be run once or several times so as to get the final product with better purity.

: The followings are data obtained by actual operation of the above steps and analysis results of infrared (IR) spectroscopy and nuclear magnetic resonance spectroscopy.

Synthesis of Anabaseine

Add 25 mL anhydrous tetrahydrofuran (THF) into a 100 ml round bottom flask and place the round bottom flask in a liquid nitrogen bath to reduce the temperature to −70° C. Then add 20 mL 1.5 M lithium diisopropylamide (LDA) dissolved in cyclohexane into the flask. Next dissolve 3 g δ-valerlactam in 25 mL anhydrous THF and add the δ-valerlactam solution drop by drop into the above solution. Then add 3.75 mL (30 mmole) trimethylsilyl chloride (TMSCl) into the solution. The solution is first stirred at −70° C. for 15 minutes, then moved to room temperature and stirred for 2 hours. Then the flask is placed into a liquid nitrogen bath for reducing the temperature to −70° C. and 20 mL 1.5 M LDA is added drop by drop into the solution. Add 2.75 mL ethyl nicotinate into the solution to get the mixed solution. Next the mixed solution is stirred at −70° C. for 15 minutes and then at room temperature for 17 hours. Add 1 mL injection water and precipitate is formed after being stirred for 15 minutes. The precipitated light yellow solid is filtered, washed with a little cold water and dried to get about 4.1 g milky white solid intermediate lithium 3-nicotinoyl-2-piperidone enolate.

Add 10 mL concentrated hydrochloric acid into a 100 ml round bottom flask and place the round bottom flask in an ice bath. Then take and add 1 g lithium 3-nicotinoyl-2-piperidone enolate into the flaks in portions. The solution is heated to reflux. After 18 hours, add pre-cooled isopropyl alcohol into the solution until the solution is down to room temperature and some solid start to precipitate. Next the solution is placed into a refrigerator overnight. Collect the product by vacuum filtration and wash the product with a certain amount of isopropyl alcohol. The product remained on filter paper is washed with water and dried. Thus 0.6 g off-white solid product 1 anabaseine (yield: 78.9%) is obtained.

Analysis of Anabaseine: $^1$H NMR (300 MHz, D$_2$O) δ(ppm): 1.64 (m, 4H, two —CH$_2$), 2.93 (t, 2H, N═C—CH$_2$), 3.10 (t, 2H, C═N—CH$_2$), 8.10 (dd, 1H), 8.85 (d, 1H), 8.97 (d, 1H), 9.20 (s, 1H); $^{13}$C-NMR (75 MHz, D$_2$O) δ(ppm): 198.3, 145.7, 144.5, 141.9, 135.1, 127.9, 38.4, 38.3, 26.2, 19.7; IR (KBr): $v_{CH}$ 1580 &1620 cm$^{-1}$ (Aromatic ring), $v_{C═N}$=1680 cm$^{-1}$.

Synthesis of 4-hydroxyethoxy-2-methoxybenz-aldehyde 2.998 g (19.7 m mole) 4-hydroxy-2-methoxybenzaldehyde and 1.201 g (21.4 m mole) potassium hydroxide are suspended in 30 mL absolute alcohol, heat to 95° C. and react for 1 hour. After cooling, add 1.5 mL (20.1 m mole) 2-bromoethanol into the solution, heat the solution to 95° C. again and react for 17 hours. After cooling, use layer chromatography (TLC) to detect whether there is any starting material unreacted in the solution. When there is some starting material unreacted, add 1.229 g (21.9 m mole) potassium hydroxide into the solution again and heat the solution to 95° C. to react for 1 hour. Then add 1.5 mL (20.1 m mole) 2-bromoethanol into the solution after cooling and then heat the solution to 95° C. to react for 24 hours. The solvent is removed after the solution being cooled down to room temperature and the crude product obtained is purified by column chromatography (eluant n-hexane/ethyl acetate (1:1) (3:7)). The liquid collected is concentrated to get 3.26 g light yellow solid product 2 (yield: 86.2%).

Analysis of 4-hydroxyethoxy-2-methoxybenz-aldehyde: H NMR (300 MHz, CDCl$_3$) δ(ppm): 10.27 (s, 1H), 7.80 (d, J=8.7 Hz, 1H), 6.56.6.53 (m, 1H), 6.49 (d, J=2.4 Hz, 1H), 4.17 (dd, J=3.9, 1.5 Hz, 2H), 4.01 (t, J=3.9 Hz, 2H), 3.89 (s, 3H); $^{13}$C-NMR (75 MHz, CDCl$_3$) δ(ppm): 188.8, 165.7, 163.9, 130.9, 119.2, 106.6, 98.7, 69.9, 61.2, 55.8; IR (KBr): $v_{CH}$=1520 & 1620 cm$^{-1}$ (Aromatic ring), $v_{C═O}$=1680 cm$^{-1}$, $v_{C═O}$=2715 cm$^{-1}$, $v_{O—H}$=3200-3400 cm$^{-1}$.

Synthesis of 4-OH substituted anabaseine derivative, 3-[(4-Hydroxyethoxy-2-methoxy)benzylidene]anabaseine Add 0.35 g (1.50 mmole) anabaseine and 0.50 g (3.29 mmole) 4-hydroxyethoxy-2-methoxybenzaldehyde into a 50 ml round bottom flask. Then add 15 mL absolute alcohol and 1 mL concentrated hydrochloric acid into the flask. The suspended solution is heated under reflux. After 18 hours, slowly add ether to the solution until the solution becomes cloudy after the solution being cooled to room temperature. The solution is placed into the refrigerator overnight. Then collect a product by vacuum filtration and wash the product with a proper amount of ether. The product remained on the filter paper is dissolved in methanol and then precipitated by ether. Repeat the step of dissolution with methanol and precipitation with ether three times. At last 0.38 g red solid product 3 (yield: 82.4%) is obtained.

Analysis of 3-[(4-Hydroxyethoxy-2-methoxy)-benzylidene]anabaseine: $^1$H NMR (300 MHz, CD$_3$OD) δ(ppm): 1.64 (m, 4H, two —CH$_2$), 2.20 (t, 2H, N═C—CH$_2$), 3.10 (t, 2H, C═N—CH$_2$), 3.35 (dd, 2H, —CH$_2$), 3.82 (s, 3H, —OCH$_3$), 3.95 (t, 2H, —CH$_2$), 4.00 (dd, 2H, —CH$_2$), 4.12 (t, 2H, —CH$_2$), 6.62 (s, 1H), 6.75 (d, 1H), 7.55 (d, 1H), 7.70 (dd, 1H), 8.15 (d, 1H), 8.63 (d, 1H), 9.15 (d, 2H); 13C NMR (75 MHz, CD$_3$OD) δ(ppm): 173.5, 166.5, 163.1, 151.0, 148.9, 146.1, 145.5, 134.2, 127.8, 127.3, 117.3, 108.1, 99.7, 71.3, 61.4, 56.7, 45.9, 25.4, 20.8.

In summary, the present invention reveals a simple method for synthesis of 4-OH substituted anabaseine derivative that minimizes loss of the final product by selection of wash solutions, columns used for isolation and purification, and solutions for precipitation of the product. Thus not only the yield of the target product is increased, the isolation and purification steps are simplified and the production rate of the target product is increased.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for synthesis of 4-OH substituted anabaseine derivative comprising the steps of:
   carrying out a nucleophilic substitution reaction of δ-valerolactam with ethyl nicotinate to get a first intermediate product;
   heating the first intermediate product under reflux with concentrated hydrochloric acid to get a product of heating under reflux;
   washing the product of heating under reflux with cold isopropyl alcohol to get anabaseine;
   deprotonating 4-hydroxy-2-methoxy-benzaldehyde with potassium hydroxide to get a second intermediate product with benzene oxidation;
   carrying out bimolecular nucleophilic substitution (Sn2 reaction) of the second intermediate product with 2-bromoethanol to get 4-hydroxyethoxy-2-methoxy-benzaldehyde; and
   reacting anabaseine with 4-hydroxyethoxy-2-methoxy-benzaldehyde under concentrated hydrochloric acid catalysis to get a final product.

2. The method as claimed in claim 1, wherein lithium diisopropylamide (LDA) is used as a reagent in the step of carrying out a nucleophilic substitution reaction.

3. The method as claimed in claim 1, wherein a solvent used in the step of carrying out a nucleophilic substitution reaction is anhydrous tetrahydrofuran (THF).

4. The method as claimed in claim 1, wherein a temperature of δ-valerolactam and of ethyl nicotinate added is ranging from −75° C. to −65° C. in the step of carrying out a nucleophilic substitution reaction.

5. The method as claimed in claim 1, wherein a period required for adding δ-valerolactam and ethyl nicotinate is ranging from 1 hour to 3 hours in the step of carrying out a nucleophilic substitution reaction.

6. The method as claimed in claim 1, wherein δ-valerolactam and ethyl nicotinate are stirred and reacted at room temperature for 16~24 hours to get the first intermediate in the step of carrying out a nucleophilic substitution reaction.

7. The method as claimed in claim 1, wherein a temperature of the first intermediate product and the concentrated hydrochloric added is 0-4° C. in the step of heating the first intermediate product under reflux.

8. The method as claimed in claim 1, wherein an equivalent ratio of potassium hydroxide to 4-hydroxy-2-methoxy-benzaldehyde is ranging from 4:1 to 1:1 in the step of deprotonating 4-hydroxy-2-methoxy-benzaldehyde with potassium hydroxide.

9. The method as claimed in claim 1, wherein 4-hydroxy-2-methoxy-benzaldehyde and potassium hydroxide are heated to 90° C.~100° C. to react in the step of deprotonating 4-hydroxy-2-methoxybenzaldehyde with potassium hydroxide.

10. The method as claimed in claim 1, wherein reaction time is ranging from 0.5 to 2 hours in the step of deprotonating 4-hydroxy-2-methoxy-benzaldehyde with potassium hydroxide.

11. The method as claimed in claim 1, wherein reaction temperature is ranging from 90° C. to 100° C. in the step of carrying out bimolecular nucleophilic substitution (Sn2 reaction).

12. The method as claimed in claim 1, wherein reaction time is ranging from 16 hours to 24 hours in the step of carrying out bimolecular nucleophilic substitution (Sn2 reaction).

13. The method as claimed in claim 8, wherein a starting material is separated and recovered by a solvent having n-hexane and ethyl acetate in a ratio of n-hexane to ethyl acetate is 1:1; then 4-hydroxyethoxy-2-methoxybenzaldehyde is separated and obtained by a solvent having n-hexane and ethyl acetate in a ratio of 3:7 after the step of carrying out bimolecular nucleophilic substitution (Sn2 reaction).

14. The method as claimed in claim 1, wherein after the step of reacting anabaseine with 4-hydroxyethoxy-2-methoxybenzaldehyde under concentrated hydrochloric acid catalysis to get a final product, the method further includes a step of dissolving the final product in methanol and then precipitating the final product with ether for increasing yield.

* * * * *